United States Patent
Zehetmaier et al.

(10) Patent No.: US 10,602,999 B2
(45) Date of Patent: Mar. 31, 2020

(54) X-RAY SYSTEM AND METHOD FOR OPERATING AN X-RAY SYSTEM

(71) Applicant: AGFA NV, Mortsel (BE)

(72) Inventors: Thomas Zehetmaier, Neufarn (DE); Johannes Hoelzl, Grasbrunn (DE); Florian Von Stein, Groebenzell (DE)

(73) Assignee: AGFA NV, Mortsel (BE)

( * ) Notice: Subject to any disclaimer, the term of this patent is extended or adjusted under 35 U.S.C. 154(b) by 158 days.

(21) Appl. No.: 15/749,529

(22) PCT Filed: Aug. 3, 2016

(86) PCT No.: PCT/EP2016/068510
§ 371 (c)(1),
(2) Date: Feb. 1, 2018

(87) PCT Pub. No.: WO2017/025400
PCT Pub. Date: Feb. 16, 2017

(65) Prior Publication Data
US 2018/0220982 A1   Aug. 9, 2018

(30) Foreign Application Priority Data

Aug. 7, 2015 (EP) .................................. 15180152

(51) Int. Cl.
*A61B 6/00* (2006.01)
(52) U.S. Cl.
CPC .......... *A61B 6/4435* (2013.01); *A61B 6/4464* (2013.01)
(58) Field of Classification Search
CPC .............................. A61B 6/4435; A61B 6/4464
See application file for complete search history.

(56) References Cited

U.S. PATENT DOCUMENTS

| | | | | |
|---|---|---|---|---|
| 4,435,830 A | * | 3/1984 | Suzuki ................. | A61B 6/4464 378/190 |
| 2011/0222667 A1 | * | 9/2011 | Gregerson ............ | A61B 6/035 378/198 |
| 2011/0268254 A1 | * | 11/2011 | Peters .................. | A61B 6/4441 378/197 |

(Continued)

FOREIGN PATENT DOCUMENTS

DE   10 2008 008 900 A1   7/2009

OTHER PUBLICATIONS

Official Communication issued in International Patent Application No. PCT/EP2016/068510, dated Oct. 27, 2016.

*Primary Examiner* — Mark R Gaworecki
(74) *Attorney, Agent, or Firm* — Keating and Bennett, LLP

(57) ABSTRACT

An X-ray system includes an X-ray source and/or an X-ray detector, at least two guide rails, and at least one carriage on which the X-ray source and/or the X-ray detector is mounted. The carriage includes first guide wheels and second guide wheels, and a drive unit including drive wheels and a motor drive that drives the one or more drive wheels. The first guide wheels move between at least two different positions relative to the carriage. In a first position, the drive wheels are in a lifted position such that the carriage is moveably mounted on the guide rails via the first and second guide wheels. In a second position, the first guide wheels disengage from the guide rails while the drive wheels engage with the guide rails such that the carriage is moveably mounted on the guide rails via the second guide wheels and the drive wheels.

8 Claims, 4 Drawing Sheets

(56) References Cited

U.S. PATENT DOCUMENTS

2012/0087479 A1     4/2012   Moon et al.
2013/0028388 A1*   1/2013   Yoshida ............... A61B 6/4441
                                                                                      378/190

\* cited by examiner

X-RAY SYSTEM AND METHOD FOR OPERATING AN X-RAY SYSTEM

CROSS REFERENCE TO RELATED APPLICATIONS

This application is a 371 National Stage Application of PCT/EP2016/068510, filed Aug. 3, 2016. This application claims the benefit of European Application No. 15180152.9, filed Aug. 7, 2015, which is incorporated by reference herein in its entirety.

BACKGROUND OF THE INVENTION

1. Field of the Invention

The present invention relates to an X-ray system and an according method for operating an X-ray system.

2. Description of the Related Art

In many X-ray systems for medical imaging an X-ray tube is mounted on an overhead support or a ceiling-mounted tube support, by which the X-ray tube can be placed into a desired position relative to a patient to be examined. The movement of the X-ray tube may be supported, e.g., by motor-driven wire rope hoists, toothed racks or toothed belts which are integrated in a ceiling-mounted rail system. In general, such drive mechanisms are difficult to retrofit into an already existing manually driven X-ray system. Moreover, the maintenance of X-ray systems having such drive mechanisms may be complex and time-consuming.

SUMMARY OF THE INVENTION

Preferred embodiments of the present invention provide an X-ray system and an according method for operating an X-ray system which overcome or at least reduce drawbacks of systems and methods according to the prior art.

The advantages and benefits are achieved by the X-ray system and the method for operating an X-ray system described below.

An X-ray system according to an aspect of the invention comprises: an X-ray source configured to generate X-ray radiation and/or an X-ray detector configured to detect X-ray radiation; at least two guide rails; at least one carriage on which the X-ray source and/or the X-ray detector is mounted, the carriage comprising first and second guide wheels; and a drive unit attached to the carriage, the drive unit comprising one or more drive wheels and a motor drive, the motor drive being configured to drive the one or more drive wheels. Preferably, the first guide wheels are adjustably mounted on the carriage and configured to be moved between at least two different positions relative to the carriage such that i) in a first position of the first guide wheels the first guide wheels rest on the guide rails, while the drive wheels of the drive unit are in a lifted position relative to the guide rails in which the drive wheels do not engage with the guide rails, whereby the carriage is moveably mounted on the guide rails via the first and second guide wheels, and ii) in a second position of the first guide wheels the first guide wheels disengage from the guide rails, while the drive wheels of the drive unit engage with the guide rails to form a frictional connection with the guide rails, whereby the carriage is moveably mounted on the guide rails via the second guide wheels and the drive wheels which are driven by the motor drive.

According to another aspect of the invention, in a method for operating an X-ray system comprising an X-ray source and/or an X-ray detector, at least two guide rails, at least one carriage on which the X-ray source and/or the X-ray detector is mounted, the carriage comprising first and second guide wheels, and a drive unit attached to the carriage, the drive unit comprising one or more drive wheels and a motor drive, the motor drive being configured to drive the one or more drive wheels, wherein the first guide wheels are adjustably mounted on the carriage, the method comprises moving the first guide wheels between at least two different positions such that i) in a first position of the first guide wheels the first guide wheels rest on the guide rails, while the drive wheels of the drive unit are in a lifted position relative to the guide rails in which the drive wheels do not engage with the guide rails, whereby the carriage is moveably mounted on the guide rails via the first and second guide wheels, and ii) in a second position of the first guide wheels the first guide wheels disengage from the guide rails, while the drive wheels of the drive unit engage with the guide rails to form a frictional connection with the guide rails, whereby the carriage is moveably mounted on the guide rails via the second guide wheels and the drive wheels which are driven by the motor drive.

An aspect of the invention is based on the approach to provide a carriage, which is moveably mounted on guide rails via guide wheels, with a drive unit comprising one or more motor-driven drive wheels. One or more of the guide wheels, also referred to as "first guide wheels", are adjustably mounted on the carriage such that their position relative to the carriage can be changed or shifted between at least two different positions. In a first position of the first guide wheels both the "passive", i.e. not motor-driven, first guide wheels and the remaining passive guide wheels, also referred to as "second guide wheels", rest on the guide rails, whereas the motor-driven drive wheels of the drive unit, which is fixedly attached to the carriage, are in a lifted position in which they have no contact and/or no frictional connection to the guide rails. If the first guide wheels are shifted into a second position, the first guide wheels are in a raised position with respect to the guide rails and disengage from the guide rails, whereas the drive wheels of the drive unit are in a lowered position in which they engage and form a frictional connection with the guide rails. In this second configuration, the carriage is mounted to the guide rails via the passive second guide wheels and the motor-driven drive wheels, whereby a movement of the carriage is supported by the motor-driven drive wheels.

By adjusting the first guide wheels in the first position, the carriage, on which the X-ray source is mounted, can be moved into the desired position only manually, while no support by the motor drive is given. However, as the drive wheels of the drive unit do not engage with the guide rails, the drive unit can be easily demounted from or mounted on the carriage for maintenance and/or retrofitting purposes. By adjusting the first guide wheels in the second position, the movement of the carriage is supported by motor-driven drive wheels in a reliably and simple way.

In summary, the invention provides an X-ray system and a method for operating an X-ray system that allows for both a simple and reliable motor-driven support of the carriage movement and easy demounting and mounting of the drive unit for maintenance and/or retrofitting purposes.

According to a preferred embodiment, at least one of the first guide wheels is mounted on the carriage by an eccentric cam. By pivoting the eccentric cam the drive wheel, which is rotatably mounted on the cam, can be swiveled from the first position into the second position, in order to move the guide wheel away from the guide rail, and/or from the second position into the first position, in order to move the guide wheel towards the guide rail. An eccentric cam allows for a particularly simple and reliable adjustment of the first guide wheel position, which further enhances the simplicity and reliability of the motor-driven support of the carriage movement and further facilitates demounting and mounting of the drive unit for maintenance and/or retrofitting purposes.

It is further preferred that the eccentric cam comprises a first shaft having a first rotational axis and a second shaft having a second rotational axis, the first shaft being fixed on the second shaft, wherein the first rotational axis is offset from the second rotational axis, the first guide wheel being rotatably mounted on the first shaft and the second shaft being rotatably mounted on the carriage. By pivoting the second shaft the drive wheel, which is rotatably mounted on the first shaft, can be swiveled from the first position into the second position, in order to move the guide wheel away from the guide rail, and/or from the second position into the first position, in order to move the guide wheel towards the guide rail.

According to another preferred embodiment, the drive unit is attached to the carriage such that the drive wheels of the drive unit are closer to the first guide wheels than to the second guide wheels. In this way, the drive wheels can be easily "lifted" off the guide rails by shifting the first guide wheels into the first position. Likewise, the drive wheels can be easily "lowered" down to the guide rails by shifting the first guide wheels into the second position. Thus, this embodiment further enhances the simplicity and reliability of the motor-driven support of the carriage movement and further facilitates demounting and mounting of the drive unit.

According to yet another preferred embodiment, the system comprises a vertical arm having an upper end and a lower end, the X-ray source and/or the X-ray detector being mounted on the lower end of the vertical arm, the upper end of the vertical arm being mounted on the carriage, wherein the upper end of the vertical arm is closer to a first end of the carriage then to an opposing second end of the carriage, and the drive unit being attached to the carriage at the first end of the carriage. In this way, it is ensured that vertical forces by which the drive wheels of the drive unit are pressed against the guide rails and the resulting frictional forces between the guide rails and the motor-driven drive wheels are particularly high. This further enhances the simplicity and reliability of the motor-driven support of the carriage movement.

According to an alternative or additional embodiment, the system comprises a vertical arm having an upper end and a lower end, the X-ray source and/or the X-ray detector being mounted on the lower end of the vertical arm, the upper end of the vertical arm being mounted on the carriage, the carriage together with the vertical arm having a center of mass, and the drive unit being attached to the carriage at a first end of the carriage, wherein the first end of the carriage is closer to the center of mass than an opposing second end of the carriage. In this way, it is ensured that vertical forces by which the drive wheels of the drive unit are pressed against the guide rails and the resulting frictional forces between the guide rails and the motor-driven drive wheels are particularly high. This further enhances the simplicity and reliability of the motor-driven support of the carriage movement.

Further advantages, aspects and examples and alternatives of the present invention will be apparent from the description of following figures.

DETAILED DESCRIPTION OF THE PREFERRED EMBODIMENTS

Figure 1:
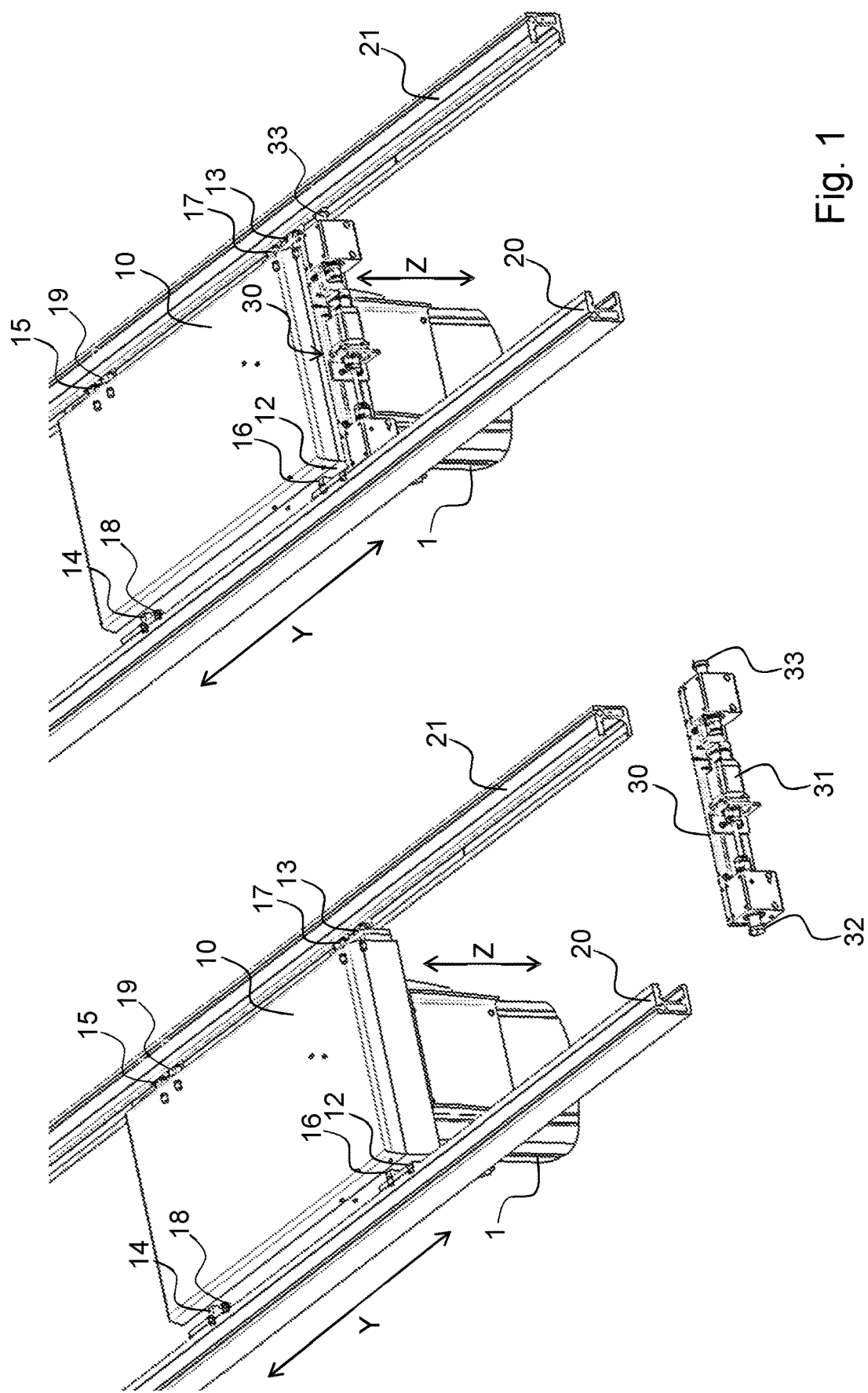
FIG. 1 is a perspective view of a section of an example of an X-ray system with demounted drive unit (left) and mounted drive unit (right).

FIG. 1 shows a perspective view of a section of an example of an X-ray system which comprises a carriage 10 which is moveably mounted on a pair of guide rails 20 and 21. A vertical telescope arm 1 is mounted on the lower side of the carriage 10 and is provided with an X-ray source (not shown) and/or an X-ray detector (not shown).

In order to place the X-ray source or the X-ray detector, respectively, into a desired position for taking an X-ray image, the carriage 10 can be moved relative to the guide rails 20 and 21 in Y-direction and/or by means of the telescope arm 1 in Z-direction.

The movement of the carriage 10 and/or the telescope arm 1 can be driven manually or by one or more motor drives. Moreover, the system can be configured such that one or more motor drives support a manually driven or manually initiated movement of the carriage 10 and/or the telescope arm 1.

For driving the movement of the carriage 10 along the pair of guide rails 20 and 21, a drive unit 30 is provided, which comprises a motor drive 31 which drives lateral drive wheels 32 and 33.

Preferably, the drive unit 30 is configured such that the drive unit 30 can be fixedly attached to a non-motorized carriage 10 of an already implemented X-ray system, i.e. an X-ray system which is already in use in a clinic or medical office, without the need of considerable design changes of the carriage 10. In this way, a non-motorized carriage 10 of an already implemented X-ray system can be retroactively equipped, i.e. retrofitted, with a drive unit 30 to motorize the movement of the carriage in a simple way.

Additionally or alternatively, the carriage 10 and/or the drive unit 30 is or are designed such that the drive unit 30, which is already fixedly mounted to the carriage 10, can be easily demounted from carriage 10.

This is illustrated in the left part of FIG. 1, showing a situation, in which the drive unit 30 is not yet mounted to the carriage 10 or has been demounted from the carriage 10. In contrast to this, in the situation shown in the right part of FIG. 1, the drive unit 30 is fixedly attached to an end of the carriage 10 such that the motor-driven drive wheels (only drive wheel 33 is partially visible, while drive wheel 32 is hidden by left guide rail 20) can engage the guide rails 20 and 21 in order to drive the carriage 10 to move in Y-direction.

In order to ensure a reliable frictional connection between the drive wheels 32 and 33 and the guide rails 20 and 21, and to allow for a simple mounting and demounting of the drive unit 30, the drive wheels 32 and 33 of the drive unit 30 and first guide wheels provided on the carriage 10 (only first guide wheel 13 is partially visible, while first guide wheel 12 is hidden by left guide rail 20) functionally interact in a manner that is described in detail in the following.

Figure 2:
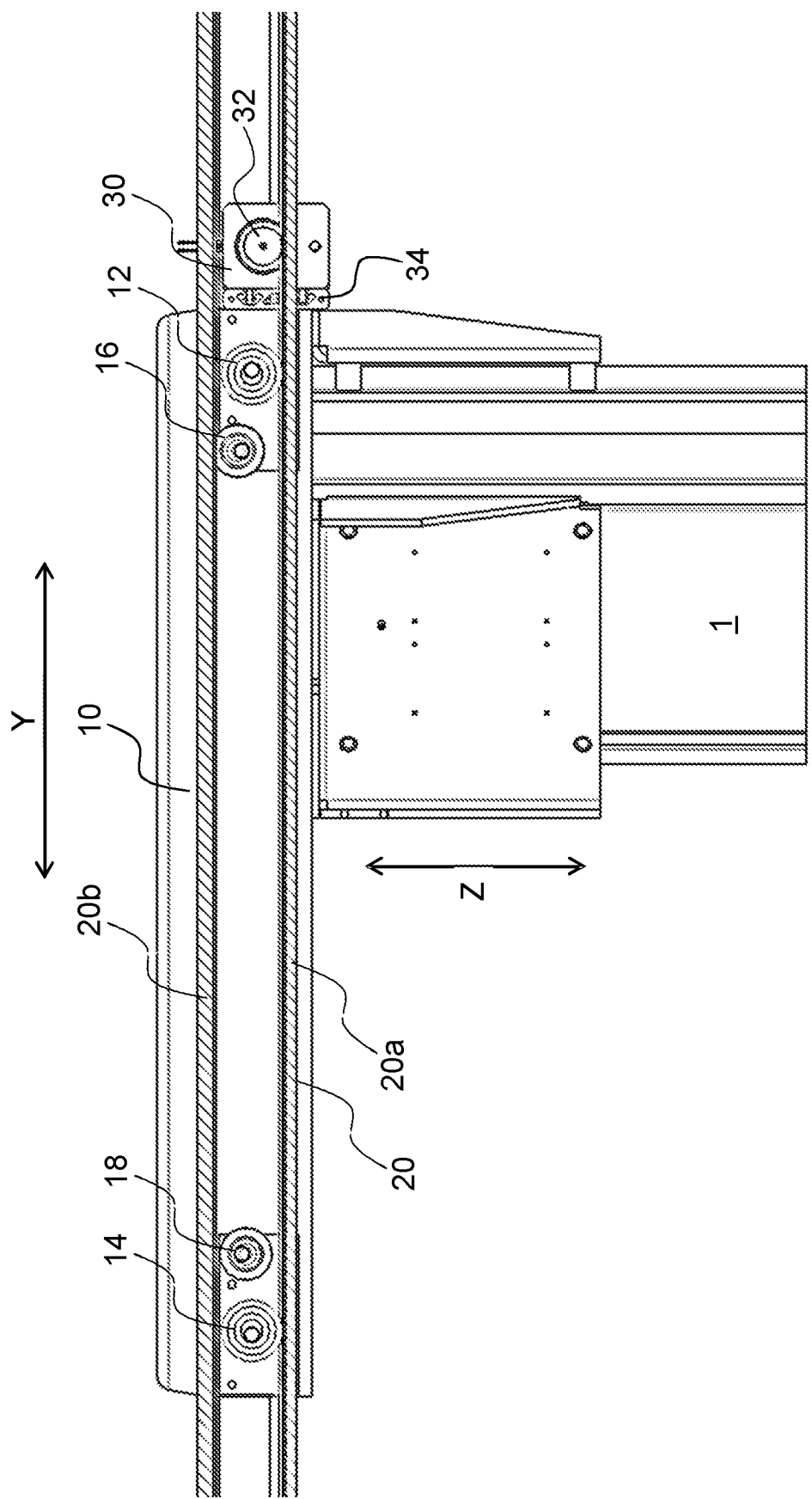
FIG. 2 is a side view of the example of an X-ray system with mounted drive unit shown in FIG. 1.

FIG. 2 shows a side view of the example of an X-ray system shown in the right part of FIG. 1. For reasons of clarity, left guide rail 20 is shown in a cross-sectional representation, in which a lower rail section 20a and an upper rail section 20b of the C-shaped guide rail 20 can be seen.

The carriage 10 is movably mounted on the lower rail section 20a of guide rail 20 via first guide wheel 12 and second guide wheel 14. Optionally, third guide wheels 16 and 18 can be provided, which engage the upper rail section 20b of guide rail 20 in order to ensure a particularly reliable guiding of the carriage 10 on guide rail 20, in particular by avoiding a derailment of the first and second guide wheels 12 and 14. Drive unit 30 is fixedly mounted to a first end of the carriage 10 by means of a mounting plate 34.

Apart from that, the explanations given in connection with the example shown in FIG. 1 apply to the example given in FIG. 2 accordingly.

Figure 3:
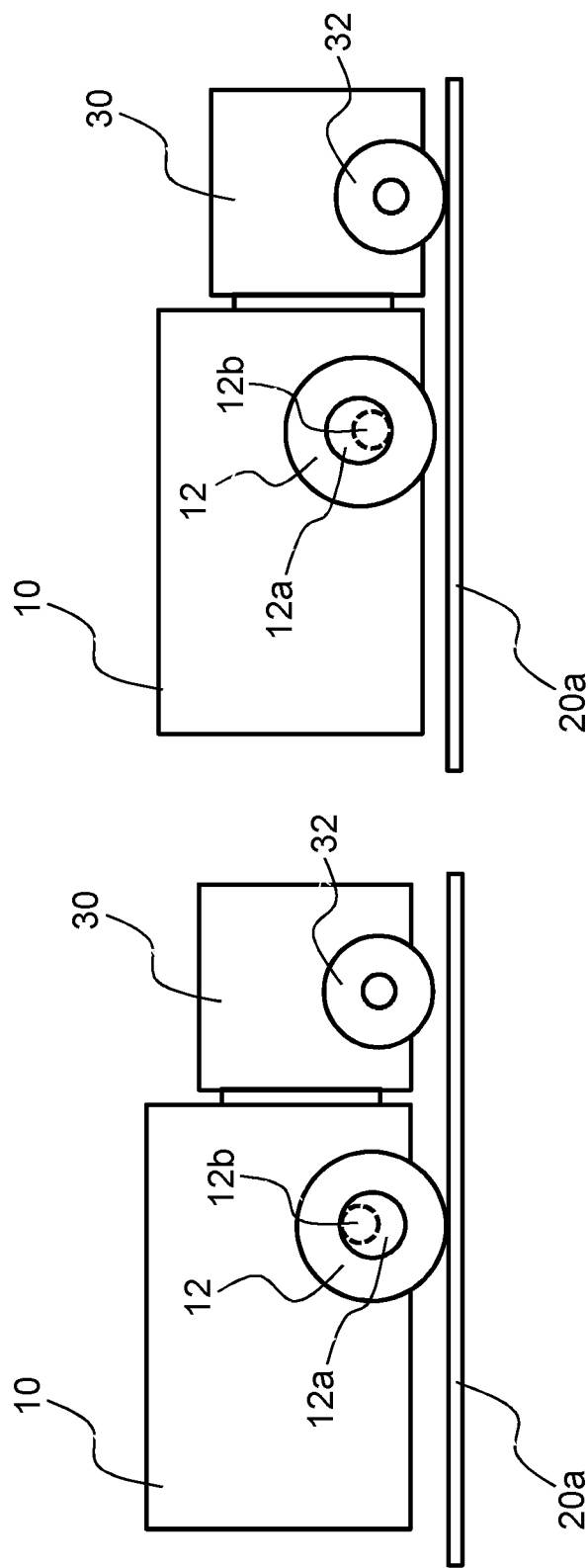
FIG. 3 is a detail of the side view of the example of an X-ray system shown in FIG. 2 with first drive wheel in a first position (left) and in a second position (right).

FIG. 3 shows a detail of the side view of the example of an X-ray system shown in FIG. 2. First guide wheel 12 is rotatably mounted on a first shaft 12a which is fixed on a second shaft 12b which is pivotably mounted on the carriage 10. The rotational axis of the first and the second shaft 12a and 12b do not coincide, i.e. the rotational axis of second shaft 12b is offset from the rotational axis of first shaft 12a. In other words, first and second shaft 12a and 12b are configured to form an eccentric cam. As a result, by pivoting shaft 12b the height of the guide wheel 12 with respect to the lower side of the carriage 10 can be varied.

Preferably, second shaft 12b is mounted on carriage 10 such that it can be pivoted into a desired angular position and fixed in this angular position. For example, the second shaft 12b is pivotably mounted in a bore (not shown) provided in a side wall of the carriage 10 and is releasably fixed on the side wall by a locking nut on a thread provided at the distal end of the second shaft 12b, i.e. at the end which is not fixed on the first shaft 12a. In order to facilitate the adjustment of the desired angular position of second shaft 12b, the distal end of second shaft 12b is preferably provided, e.g., with a hexagonal shaft end that can be turned with the aid of a hex driver. After adjusting the desired angular position of second shaft 12b, the locking nut is tightened to fix the shaft 12b in the desired angular position.

In the situation shown in the left part of FIG. 3, the rotational position of second shaft 12b is adjusted such that the guide wheel 12 has a maximum height with respect to the lower side of the carriage 10. As a result, the guide wheel 12 rests on the lower section 20a of guide rail 20, whereas drive wheel 32 of drive unit 30 remains in a lifted position slightly above the lower section 20a of the guide rail 20. By pivoting second shaft 12b in a clockwise direction, for example by approximately 180°, the carriage 10 together with the drive unit 30 that is fixedly mounted on the carriage 10 are lowered towards the lower section 20a of the guide rail 20, so that drive wheel 32 of the driving unit contacts and rests on the lower section 20a and forms a frictional connection thereto, whereas first guide wheel 12 is in a lifted position in which it no longer contacts the lower section 20a of guide rail 20.

By changing the position of first guide wheel 12, in particular by means of an eccentric cam described in detail above, a frictional connection between motor-driven drive wheel 32 of drive unit 30, on the one hand, and lower section 20a of the guide rail 20, on the other hand, can be established or suspended depending on the particular requirements of the situation.

For example, when an already existing non-motorized carriage 10 has to be provided with a driving unit 30, the guide wheel 12 is brought to an "elevated" position like the one shown in the left part of FIG. 3 so that driving unit 30 can be conveniently mounted onto the first end of the carriage 10 without any interaction between drive wheel 32 and lower section 20a of guide rail 20. Same applies accordingly for an already motorized X-ray system according to the invention in situations where the drive unit 30 has to be changed and/or maintenance work has to be carried out. Once the drive unit 30 has been fixedly mounted to carriage 10 or exchanged by another one or maintenance work has been completed, the position of the first guide wheel 12 can be changed by simply pivoting second shaft 12b into a rotational position in which the first guide wheel 12 has a "retained" position with respect to the lower side of carriage 10, whereby drive wheel 32 of the drive unit engages the lower section 20a of guide rail 20 and forms a frictional connection thereto (see right part of FIG. 3).

Preferably, at least two guide wheels 12 and 13 are provided on opposite sides of the carriage 10 (as indicated in FIG. 1) in order to ensure that left and right drive wheels 32 and 33 are more or less equally lifted from or lowered towards the respective lower sections of the left and right guide rail 20 and 21.

It is further preferred that the telescope arm 1 is mounted on the carriage 10 such that the upper end of the telescope arm 1 is closer to the first end of the carriage 10, to which the drive unit 30 is attached, than to an opposing second end of the carriage 10, which is close to the non-driven second guide wheels 14 and 15. In this way it is ensured that the vertical weight forces, by which the drive wheels 32 and 33 of drive unit 30 are pressed on guide rails 20 and 21, and the resulting frictional forces between the motor-driven drive wheels 32 and 33 and the guide rails 20 and 21 are particularly high. Additionally or alternatively, the center of mass of carriage 10 and telescope arm 1 is closer to the first end of the carriage 10, to which the drive unit 30 is attached, than to an opposing second end of the carriage 10, being close to the non-driven second guide wheels 14 and 15.

Apart from that, the explanations given in connection with the example shown in FIGS. 1 and 2 apply to the example given in FIG. 3 accordingly.

Figure 4:
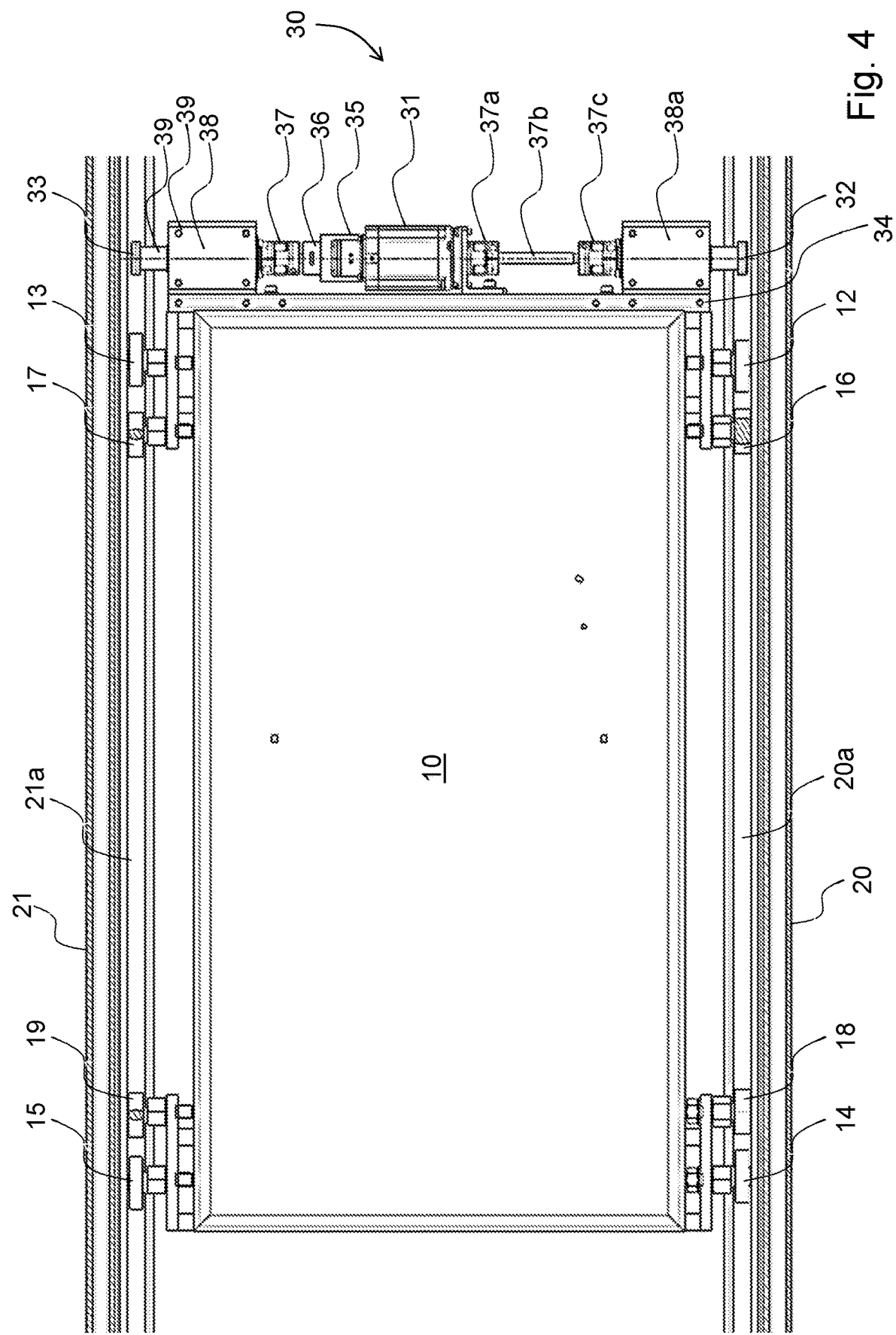
FIG. 4 is a top view of the example of an X-ray system shown in FIGS. 1 to 3.

FIG. 4 shows a top view of the example of an X-ray system shown in FIGS. 1 to 3. In order to enhance clarity, the guide rails 20 and 21 are shown in a cross-sectional representation.

As already explained above, the carriage 10 is mounted on lower sections 20a and 21a of the guide rails 20 and 21 via first guide wheels 12 and 13 and second guide wheels 14 and 15. Optionally, third guide wheels 16 to 19 can be provided which are configured to engage upper sections of the guide rails 20 and 21.

Drive unit 30 is fixedly coupled to a first end of the carriage 10 via mounting plate 34. The driving unit 30 comprises an electrical motor 31 the output shaft of which is coupled to a motor brake 35, a positional encoder 36 and a clutch 37 the output shaft of which is coupled to a bearing lock 38 comprising, for example, two ball bearings by which wheel shaft 39 of drive wheel 33 is supported. Similarly, another output shaft of motor 31 is coupled via clutch 37a, shaft extension 37b and clutch 37c to bearing block 38a by which the shaft of drive wheel 32 is supported.

Apart from that, the explanations given in connection with the example shown in FIGS. 1 to 3 apply to the example given in FIG. 4 accordingly.

The invention claimed is:

1. An X-ray system comprising:
   an X-ray source that generates X-ray radiation and/or an X-ray detector that detects X-ray radiation;
   at least two guide rails;
   a carriage on which the X-ray source and/or the X-ray detector is mounted, the carriage including first guide wheels and second guide wheels; and
   a drive unit attached to the carriage, the drive unit including one or more drive wheels and a motor drive that drives the one or more drive wheels; wherein
   the first guide wheels are adjustably mounted on the carriage to move between at least two different positions relative to the carriage such that:
      in a first position of the first guide wheels, the first guide wheels rest on the guide rails, while the drive wheels of the drive unit are in a lifted position relative to the guide rails in which the drive wheels do not engage with the guide rails, such that the carriage is moveably mounted on the guide rails via the first guide wheels and the second guide wheels; and
      in a second position of the first guide wheels, the first guide wheels disengage from the guide rails, while the drive wheels of the drive unit engage with the guide rails to establish a frictional connection with the guide rails, such that the carriage is moveably mounted on the guide rails via the second guide wheels and the drive wheels driven by the motor drive.

2. The X-ray system according to claim 1, wherein at least one of the first guide wheels is mounted on the carriage by an eccentric cam.

3. The X-ray system according to claim 2, wherein the eccentric cam includes a first shaft having a first rotational axis and a second shaft having a second rotational axis;
   the first shaft is fixed on the second shaft;
   the first rotational axis is offset from the second rotational axis; and
   the first guide wheel is rotatably mounted on the first shaft, and the second shaft is rotatably mounted on the carriage.

4. The X-ray system according to claim 1, wherein the drive unit is attached to the carriage such that the drive wheels of the drive unit are closer to the first guide wheels than to the second guide wheels.

5. The X-ray system according to claim 1, further comprising:
   a vertical arm including an upper end and a lower end; wherein
   the X-ray source and/or the X-ray detector is mounted on the lower end of the vertical arm, and the upper end of the vertical arm is mounted on the carriage;
   the upper end of the vertical arm is closer to a first end of the carriage than to an opposing second end of the carriage; and
   the drive unit is attached to the carriage at the first end of the carriage.

6. The X-ray system according to claim 1, further comprising:
   a vertical arm including an upper end and a lower end;
   the X-ray source and/or the X-ray detector is mounted on the lower end of the vertical arm, and the upper end of the vertical arm is mounted on the carriage;
   the carriage and the vertical arm together have a center of mass;
   the drive unit is attached to the carriage at a first end of the carriage; and
   the first end of the carriage is closer to the center of mass than an opposing second end of the carriage.

7. A method for operating an X-ray system, the X-ray system including:
   an X-ray source and/or an X-ray detector;
   at least two guide rails;
   a carriage on which the X-ray source and/or the X-ray detector is mounted, the carriage including first guide wheels and second guide wheels; and
   a drive unit attached to the carriage, the drive unit including one or more drive wheels and a motor drive that drives the one or more drive wheels, the first guide wheels being adjustably mounted on the carriage;
   the method comprising the steps of:
   moving the first guide wheels to a first position in which the first guide wheels rest on the guide rails, while the drive wheels of the drive unit are in a lifted position relative to the guide rails in which the drive wheels do not engage with the guide rails, such that the carriage is moveably mounted on the guide rails via the first guide wheels and the second guide wheels; and
   moving the first guide wheels to a second position in which the first guide wheels disengage from the guide rails, while the drive wheels of the drive unit engage with the guide rails to establish a frictional connection with the guide rails, such that the carriage is moveably mounted on the guide rails via the second guide wheels and the drive wheels driven by the motor drive.

8. The method according to claim 7, wherein the first guide wheels are moved between the first position and the second position by pivoting an eccentric cam by which the first guide wheels are mounted on the carriage.

* * * * *